(12) United States Patent
Liu et al.

(10) Patent No.: US 6,326,214 B1
(45) Date of Patent: Dec. 4, 2001

(54) IMMUNITY TESTING DEVICE

(76) Inventors: Yung Hsiang Liu; Wing-yee Chan, both of 6F, No. 81, Sec. 3 Cheng-Kung Rd., Taipei (TW)

( * ) Notice: Subject to any disclaimer, the term of this patent is extended or adjusted under 35 U.S.C. 154(b) by 0 days.

(21) Appl. No.: 09/261,753

(22) Filed: Mar. 3, 1999

(30) Foreign Application Priority Data

Mar. 4, 1998 (TW) .............................................. 87203118 U
Feb. 3, 1999 (TW) ..................................... 87203118A01 U

(51) Int. Cl.$^7$ ................................................. G01N 33/543
(52) U.S. Cl. .............................. 436/518; 422/56; 422/57; 422/58; 422/60; 422/61; 435/7.1; 435/7.93; 435/7.94; 435/287.7; 435/287.8; 435/287.9; 435/805; 435/810; 435/969; 435/970; 435/975; 436/518; 436/530; 436/541; 436/810; 436/823; 436/66
(58) Field of Search ................................. 422/58, 56, 61, 422/57, 60; 435/7.1, 7.93, 7.94, 287.7, 287.8, 287.9, 805, 810, 969, 970, 975; 436/518, 66, 530, 541, 810, 823

(56) References Cited

U.S. PATENT DOCUMENTS

| 1,926,299 | * | 9/1933 | Monk . |
| 3,078,031 | * | 2/1963 | Kauffeld . |
| 3,122,301 | * | 2/1964 | Barr . |
| 3,186,623 | * | 6/1965 | Guyer . |
| 3,307,770 | * | 3/1967 | Wysocki . |
| 3,951,332 | * | 4/1976 | Torbeck . |
| 3,996,006 | * | 12/1976 | Pagano . |
| 4,225,557 | * | 9/1980 | Hartl et al. . |
| 4,285,461 | * | 8/1981 | Meyers . |
| 4,464,552 | * | 8/1984 | Pawlowski . |
| 4,717,656 | * | 1/1988 | Swanljung . |
| 4,789,629 | * | 12/1988 | Baker et al. . |
| 4,803,048 | * | 2/1989 | Nason . |
| 4,962,043 | * | 10/1990 | Nagase et al. . |
| 4,976,354 | * | 12/1990 | Levy . |
| 5,143,210 | * | 9/1992 | Warwick et al. . |
| 5,182,191 | * | 1/1993 | Fan et al. . |
| 5,234,813 | * | 8/1993 | McGeehan et al. . |
| 5,441,698 | * | 8/1995 | Norell . |
| 5,747,351 | * | 5/1998 | Hemmati . |
| 5,939,252 | * | 8/1999 | Lennon et al. . |
| 5,948,687 | * | 9/1999 | Cleator . |
| 5,998,220 | * | 12/1999 | Chandler . |

FOREIGN PATENT DOCUMENTS

0653639-A1  *  5/1995  (EP) .

* cited by examiner

Primary Examiner—Bao-Thuy L. Nguyen
(74) Attorney, Agent, or Firm—Dougherty & Troxell

(57) ABSTRACT

An immunity testing device formed of a thin sheet of material folded to three portions, and the two end portions; named "front cover"0 and "back cover"; fold back to different sides of the center part; named base seat; to provide protection on both sides of the base seat. Two absorbent sheets bridged with a test paper are fixed on the side of base seat that's facing the front cover. A hole is present at the position of the first absorbent sheet on base seat for specimen application. The front cover is disposed with observation cover plates at the position corresponding to the test paper and/or water-absorbing sheets for observation of test result as well as for preventing pollution before, and after use. The test paper is pre-embedded with antibodies/antigens to capture the corresponding antigens/antibodies in the test specimen as in Immunity method. The used testing device can be burned down to ensure environmental protection. The first water-absorbent sheet may be extended into part of the unfolding area under the observation cover plate for chemical testing in addition to immunological test method, therefor, dual methods testing is achieved.

9 Claims, 11 Drawing Sheets

IMMUNITY TESTING DEVICE

BACKGROUND OF THE INVENTION

The invention is an improved Immunity Testing Device which consists of a thin sheet of material folded to three portions, and the two end portions (named "front cover" and "back cover" hereinafter) fold back to different sides of the center part (named base seat hereinafter) which supplies a complete protection for the base seat. The testing device easily achieves both immunological method and chemical method without polluting the environment. The invention also greatly reduces the production cost in comparison with the conventional device production. In all, it takes less storage space, provides more versatility, it is more economic in terms of manufacturing cost and bench labor. It is also more environmental friendly.

FIG. 1 shows a conventional immunity testing device which includes an outer case 10, an internal storage pad 11, a first filter element 12, a second filter element 13 and a wicking membrane 14. The outer case 10 is drilled with a hole 15 above the storage pad 11 and a window 18 directly positioned above a test index section 16 and a test index comparison section 17.

In use, a liquid test sample is added through the drilled hole 15 to be absorbed by the storage pad 11. Then the test sample moves and passes through the first and second filter elements 12, 13 containing a certain amount of labeled test agent. Most of the unwanted substance are filtered by the two filter elements. The remaining components continuously pass into the wicking membrane 14.

In the case that a labeled tested component exists in the test sample, the test sample will bond with the test index section 16. The remaining labeled test agent will combine with the test index comparison section 17. Through the window 18, the result of the index sections 16, 17 can be observed.

Some shortcomings exist in the above conventional immunity testing device are as follows:

1. Prior to use, the drilled hole 15 and the window 18 of the immunity testing device are not shielded and are likely to be imbued with external contaminant. This will reduce the accuracy of the test or even destroy the test result. to high cost and fails to meet the requirement of environmental protection.
2. After use, the storage pad 11 and the wicking membrane 14 of the conventional immunity testing device will contain biohazard waste carrying bacteria or viruses. Without shielding, they tend to contaminate the environment. In addition, the outer casw 10 is generally made of plastic and can be hardly destroyed. Also, the outer case 10 contains therein pollutants and thus cannot be recycled. This leads to high cost and fails to meet the requirement of enviromental protection.
3. The relatively complicated manufacturing procedure of the conventional test device contributes to its high cost, which greatly decreases the accessibility of the test.
4. The complicated design of the outer case of the conventional testing device requires much room and is rigid without the possibility of bending. Therefore, it is inconvenient to carry, store or to use the testing device.
5. With respect to overcoming the problem of false positive result in the test of human Hb, the single monoclonal immunity testing method can achieve remarkable effect. However, with respect to the test of human Heme from the disease of upper digestive organ, such method is not efficient and thus is not applicable. Therefore, a general test must be performed in cooperation with another chemical test 80 as to accomplish a boarder medical evaluation. However, there is no testing device on the market that combines both of chemical method and immunity method in one single device. As a result, the above two kinds of tests must be performed separately. This incurs a higher cost of the test as well as complication the bench work and makes the test time-consuming.

SUMMARY OF THE INVENTION

The primary object of the present invention is to provide a simple immunity testing device formed of a thin sheet instead of the conventional plastic-made case. The thin sheet of material is folded to three equal portions, the "front cover" and "back cover" fold back to different sides of the base seat to provide protection shields to both faces of the base seat from contaminants prior to use, as well as to prevent biohazardous pollution after use. Moreover, the complete device can be burnt down to ash as its nature. In general, it provides greater safety before, during, and after use.

A second object of the present invention is to use a thin, light and flexible material to provide convenience in use, carrying, and storage.

It is still a further object of the present invention to improve the conventional immunity testing procedure by providing additional chemical methodology on the same test strip, This "two in one" test device greatly increases the practicality, convenience, and economic efficacy of the test.

The present invention can be best understood through the following description and accompanying drawings, wherein:

DETAILED DESCRIPTION OF THE PREFERRED EMBODIMENTS

Figure 1:
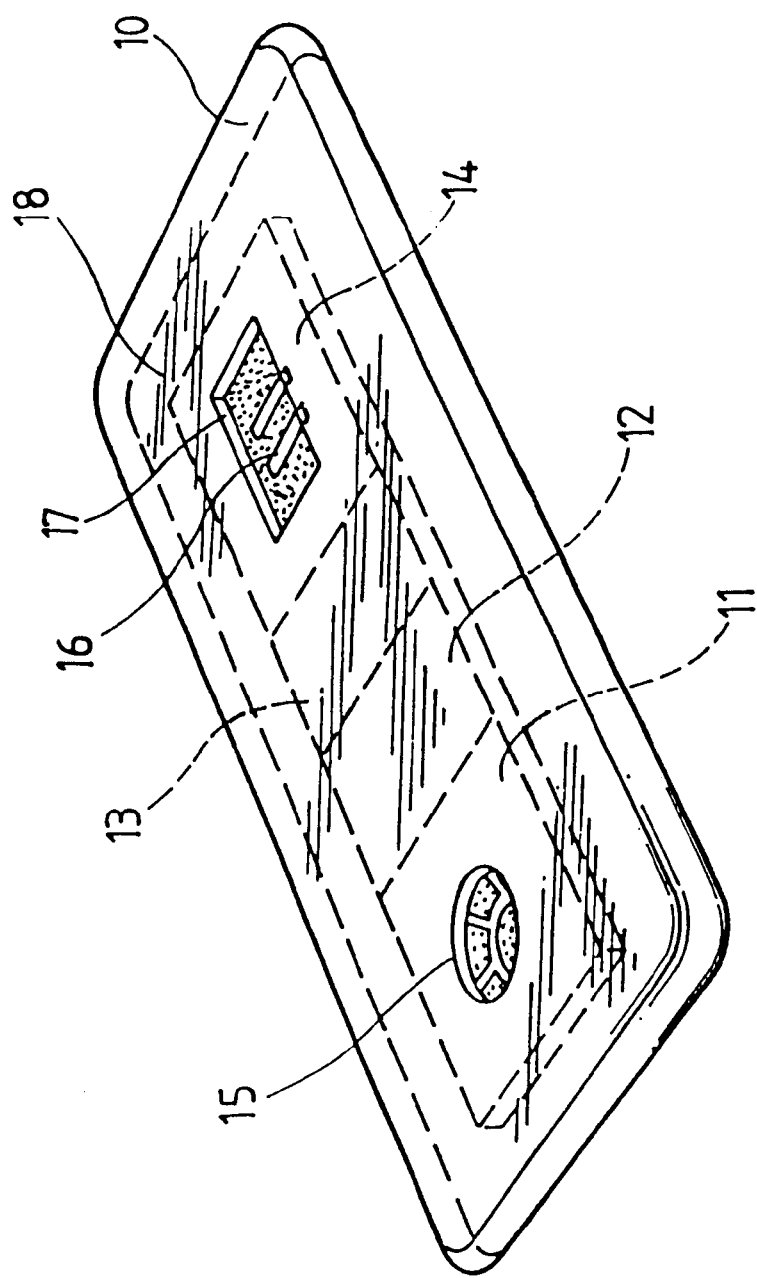
FIG. 1 is a perspective view of a conventional immunity testing device.
Figure 2:
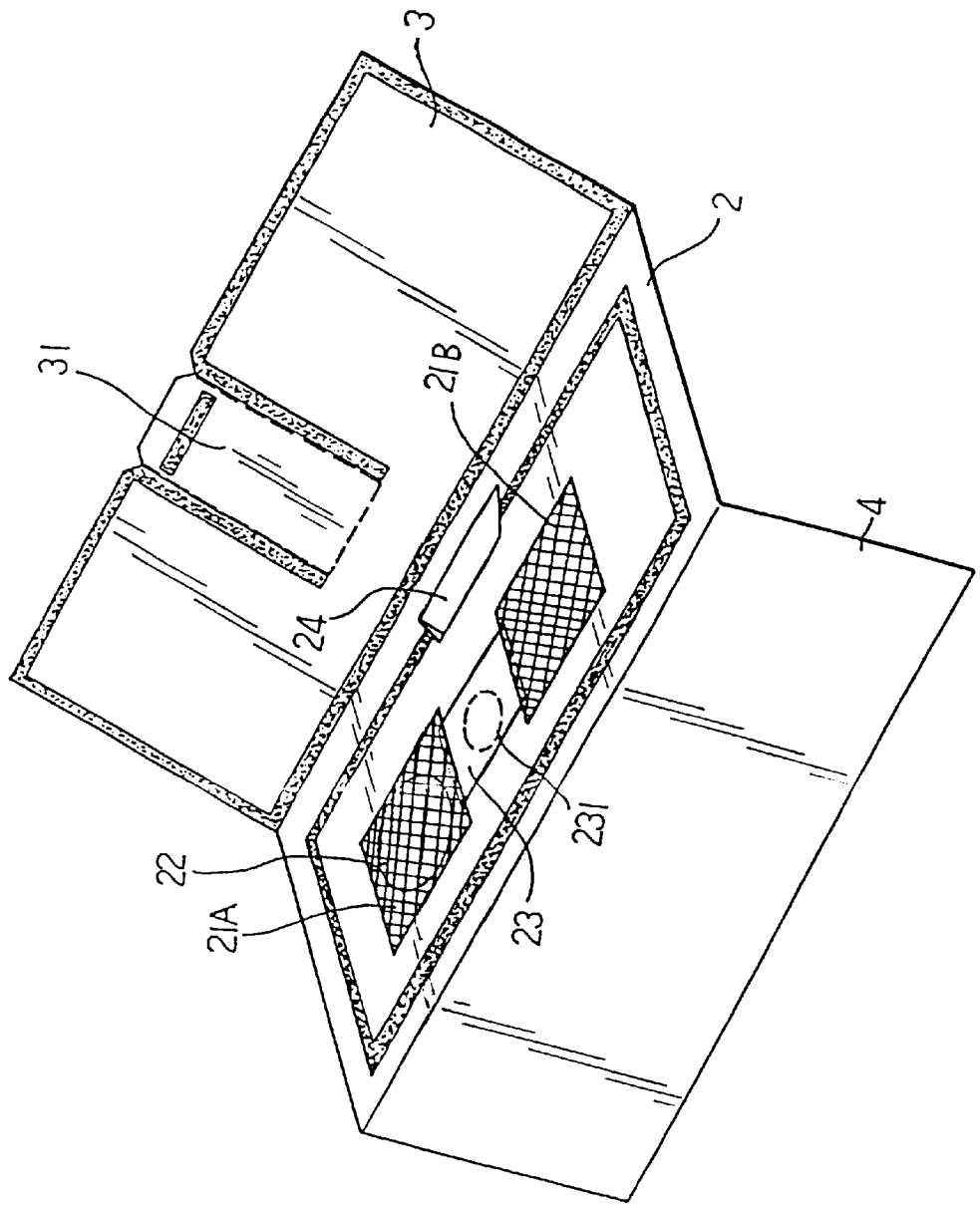
FIG. 2 is a perspective unfolded view of a first embodiment of the immunity testing device of the present invention.
Figure 3:
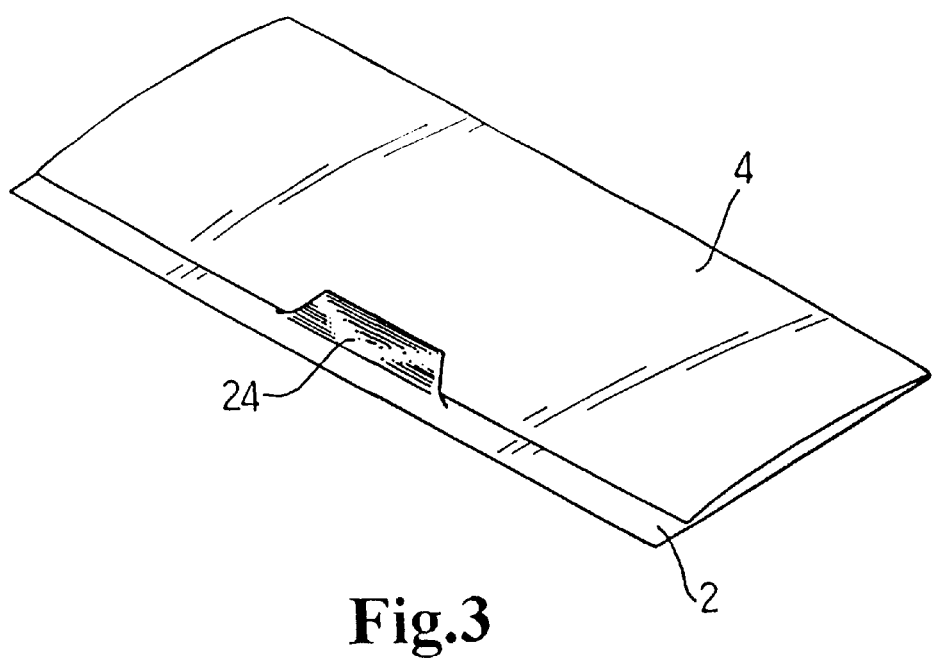
FIG. 3 is a perspective folded view of the first embodiment of the immunity testing device of the present invention, in which the front and back covers are overlaying the base seat.

Please refer to FIGS. 2 to 5. The immunity testing device of the present invention is made of a thin sheet which is folded to three equal portions, the "front cover" 3 and "back cover" 4 fold back to different sides of the base seat 2. In order to achieve a good shield protection, a certain portion of the base seat 2 and the corresponding portions of the front and back covers 3, 4 are painted with a certain amount of adhesive, whereby the base seat 2 can be well overlaid with front cover 3 and back cover 4. Alternatively, the overlaying can be assured by fastening members. On the side of base seat 2 that is facing front cover 3, attached two absorbent sheets (21A & 21B) bridged with one piece of test paper 23. Antibodies or antigens 231 are previously embedded on the test paper 23. (The embeding area can be circular, linear or other readable shape. The area is circular in this embodiment.) The test paper 23 is used to test whether the passing test sample contains the target antigens or antibodies. The front cover 3 is disposed with an observation cover plate 31 corresponding to the position of test paper 23, which can be torn apart or lifted open. When the base seat 2 in overlaid with the front cover 3, the test cover plate 31 of the front cover 3 can be lifted open for observing the development status of the test paper 23. In addition, a dripping hole 22 on the base seat 2 in the size that's no bigger than the absorbent sheet 21A is positioned in correspondence with absorbent sheet 21A, that means, the absorbent sheet 21A is covering the dripping hole 22. Users can apply the test sample 5 through the dripping hole 22 onto the first water-absorbing sheet 21A from the side of base seat 2 that is facing back cover 4. In order to facilitate the overlaying of the back cover 4 to the base seat 2, a fastening member 24 is disposed between the base seat 2 and the back cover 4. When applying test sample 5 onto the dripping hole 22 an the base seat 2, fastening member 24 is released to allow the unfolding of back cover 4 from base seat 2 for application of the test sample 5. After the application, when the base seat 2 is overlapped and fastened with the back cover 4, the fastening member 24 serves to stably fasten the back cover 4 on the base seat 2 without unexpected unfolding. This aids in keeping stable the content to be tested.

Figure 4:
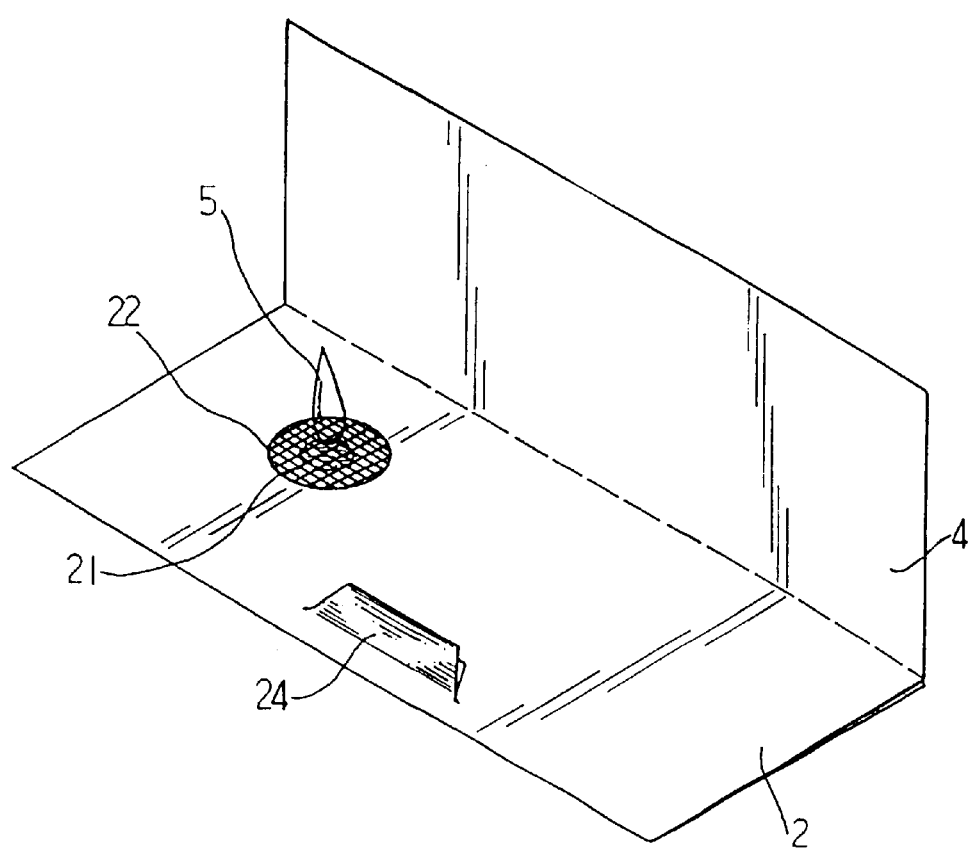
FIG. 4 is a perspective view of the first embodiment of the immunity testing device of the present invention, in which the back cover is unfolded from the base seat.
Figure 5:
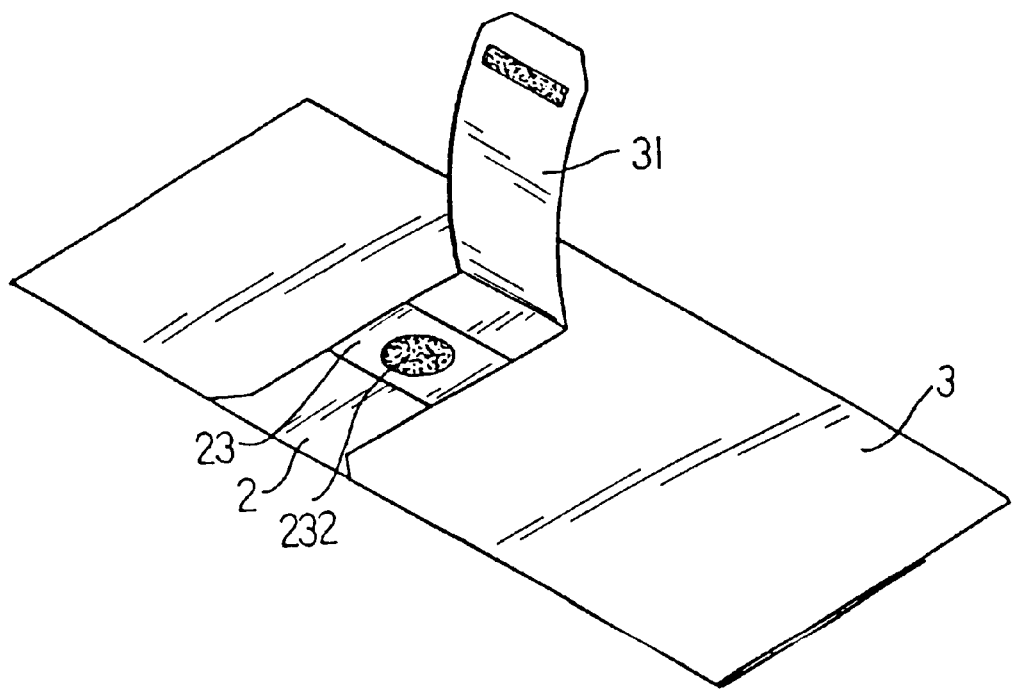
FIG. 5 is a perspective view of the first embodiment of the immunity testing device of the present invention, in which the observation cover plate on a front cover is unfolded from the base seat.

In use, as shown in FIG. 4, the back cover 4 originally overlaying the base seat 2 by the fastening member 24 is unfolded open. Then the test sample 5 is dripped through the dripping hole 22 onto the first water-absorbing sheet 21A. Then the back cover 4 is recapped back on the base seat 2. Within a specific period of time, the test sample 5 diffuses from the first water-absorbing sheet 21A through the test paper 23 to the second water-absorbing sheet 21B at the other end. During this procedure, in the case that the test sample contains a target tested component (such as human Hb), it will be bound to the previously embedded antibody or antigen. Then users only needs to unfold open the observation cover plate 31 on the front cover 3 and drip in a test agent (such as hydrogen peroxide and guaiaconic acid) so as to observe any visible changes of colour 232 on test paper 23 which is an index of the test result. After use, the observation cover plate 31 is again overlapped with the base seat 2 so as to avoid contamination of the environment. Also, the immunity testing result can be stably maintained. In addition, the testing material can be easily burnt down without biohazardous pollution of the environment. Prior to use, the testing device prevents contamination. Prior to use, the testing device is uneasy to be intruded and by external article to affect the accuracy of the test. The above testing device has simple structure so that the manufacturing cost is reduced and the product can be popularized.

It should be noted that the adhesive and fastening member for the above bass seat 2 and cover bodies 3, 4 are only some preferred embodiments of the present invention and can be modified in different pattern and position as necessary.

As shown in FIGS. 8 to 11, the first water-absorbing sheet 21A is partially elongated to extend into an unfolding area 21C which is under the cover of the observation cover plate 31. Accordingly, after applying the test sample 5, a test agent can be added on area 21C for chemical test performance, to achieve dual test results.

In use, the back cover 4 originally overlaying the base seat 2 by the fastening member 24 is unfolded open. Then the test sample 5 is dripped through the dripping hole 22 onto the first water-absorbing sheet 21A and 21C. Then the back cover 4 is recapped back on the bass seat 2. Within a specific period of time, the test sample 5 diffuses from the first water-absorbing sheet 21A and 21C through the test paper 23 to the second water-absorbing sheet 21B at the other and. During this procedure, in the case that the test sample contains an target tested component (such as human Hb), it will be bound onto the previously embedded antibody or antigen. Then a user only needs to unfold open the observation cover plate 31 on the front cover 3 and drip in a test agent (such as hydrogen peroxide and guaiaconic acid). At this time, the test agent will react with the target tested article (such as human Hb) bound on the antibody or antigen embedded on the test paper 23 so an to create a visible development change 232 (which can be in various profiles as designed). This is a positive result of immunity method. In the case that there is no development change, this means a negative result. In addition, the test agent dripped onto the test paper 23 Will simultaneously spread into the first water-absorbing sheet 21C to react with the second target tested article (such as human Heme) at this position to create visible development change. This means a positive result of chemical method. In the case of no development change, this means a negative result for the chemical reaction.

Therefore, when dripping the teat agent into the test paper 23 and after a specific period of reaction time, a user can observe whether the test paper 23 has a development change 232 so as to judge whether the test sample 5 contains the target element. This is the single monoclonal immunity testing method. In addition, the user can simultaneously observe the section 21C which is the extension of the first sheet 21A into the unfolding area under the observation cover plate 31 for observation of any development change. This is the chemical method test. In conclusion, this present invention achieves both immunological and chemical testing methods in one device, one step for a broader evaluation of the test sample. This feature saves big for both manufacturing cost and bench labor.

Figure 6:
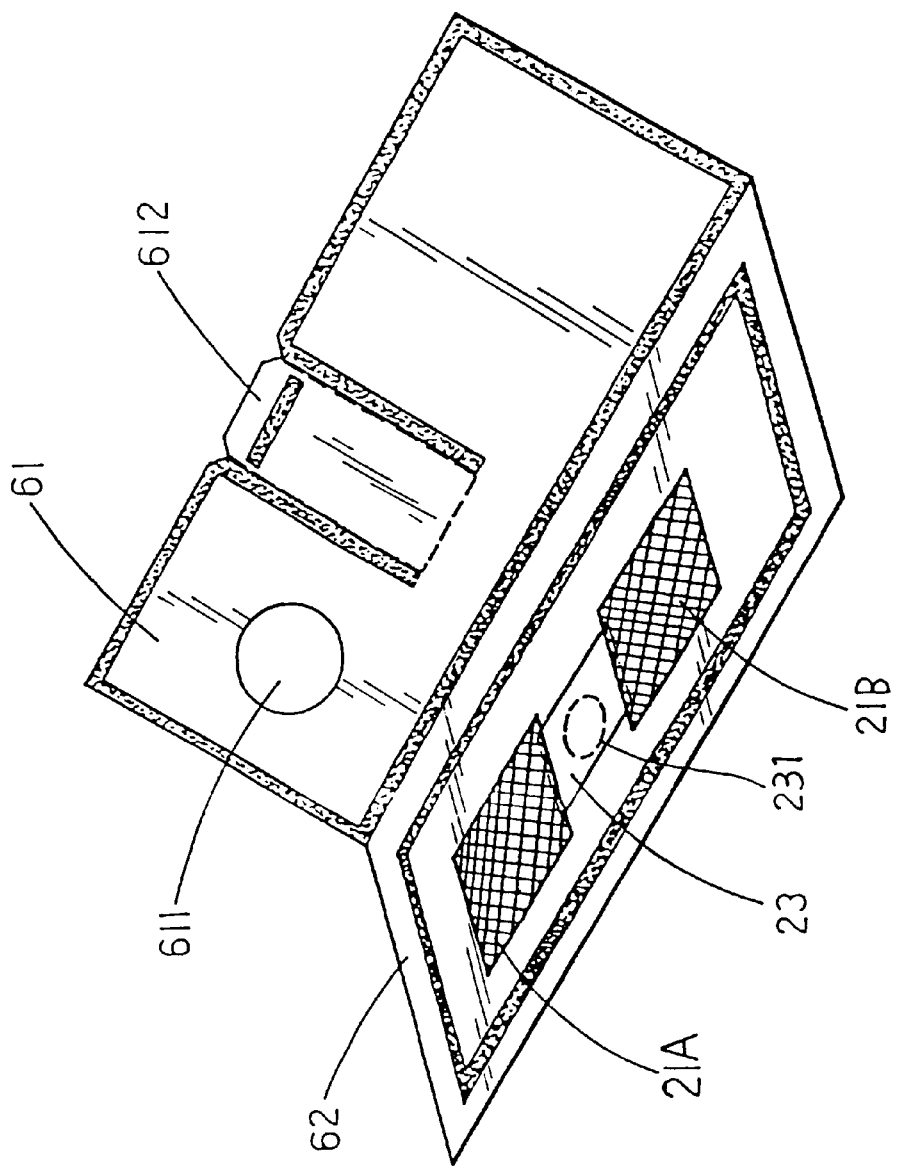
FIG. 6 is a perspective unfolded view of a second embodiment of the immunity testing device of the present invention.
Figure 7:
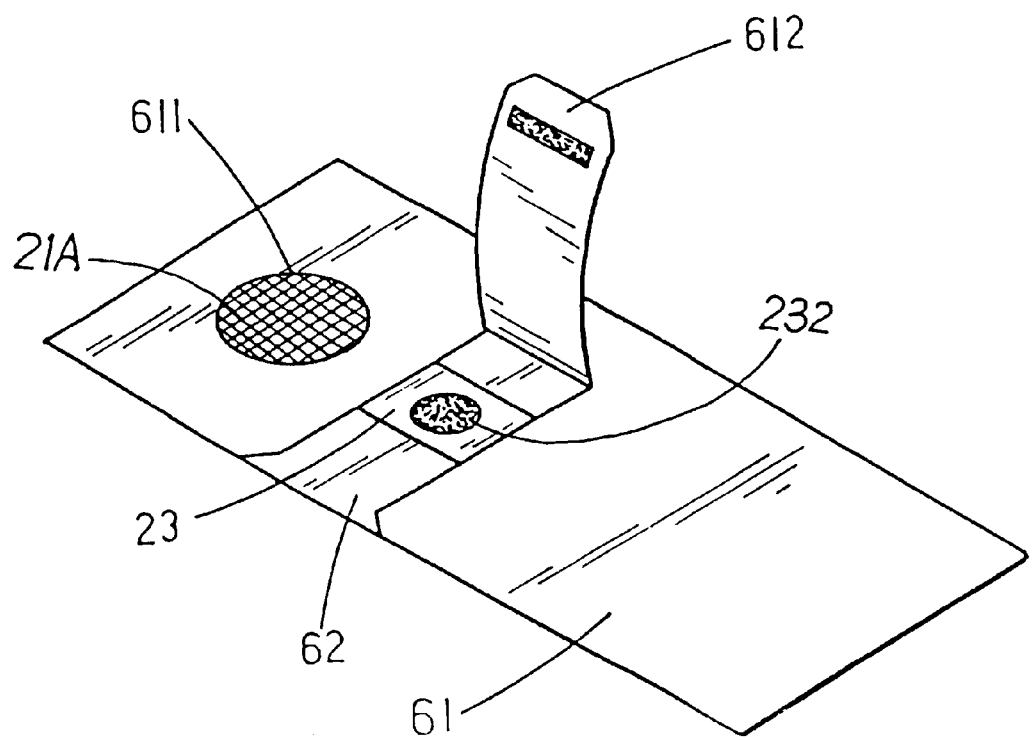
FIG. 7 is a perspective view of the second embodiment of the immunity testing device of the present invention, in which the observation cover plate is unfolded from the base seat.
Figure 8:
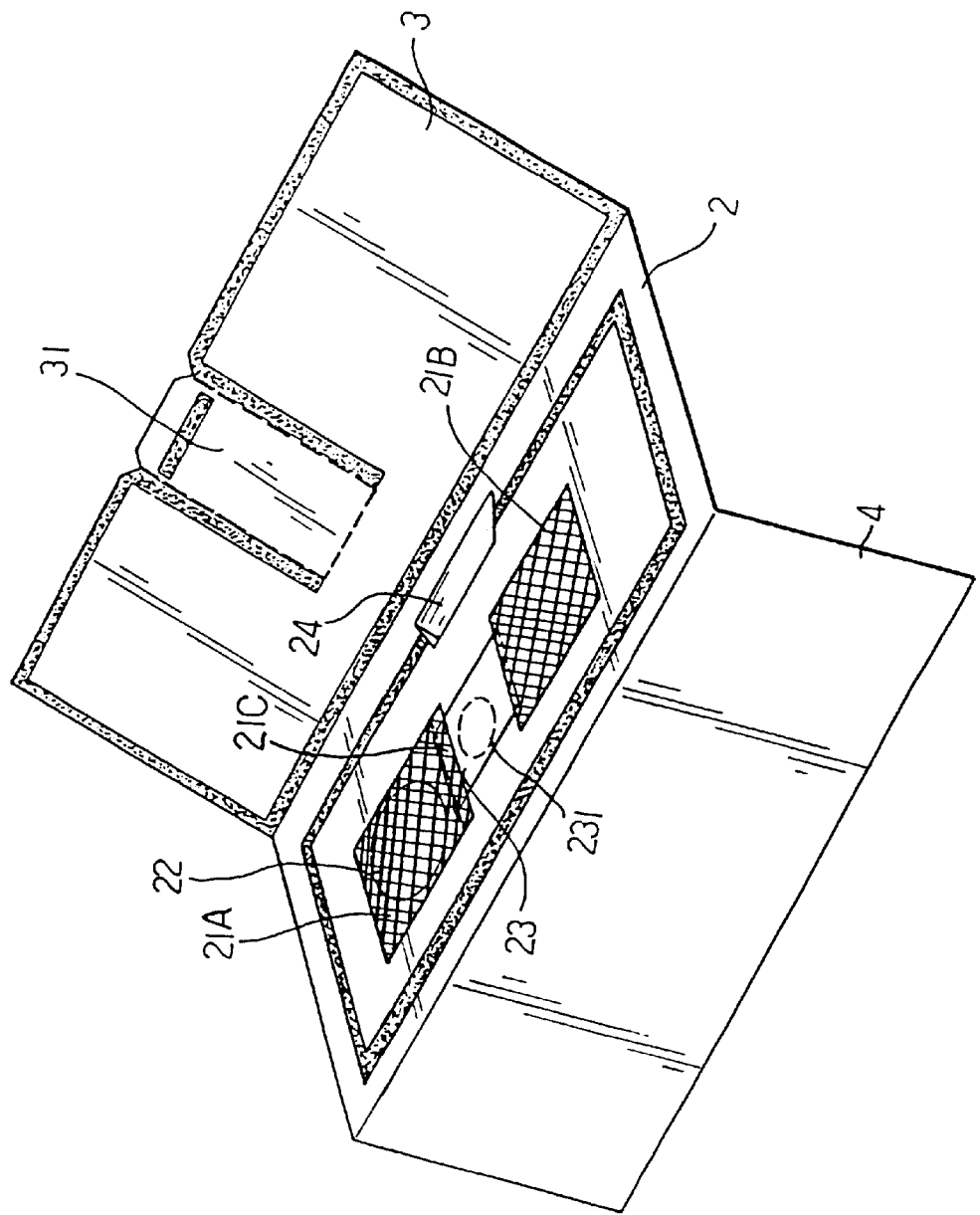
FIG. 8 is a perspective unfolded view of a third embodiment of the immunity testing device of the present invention.
Figure 9:
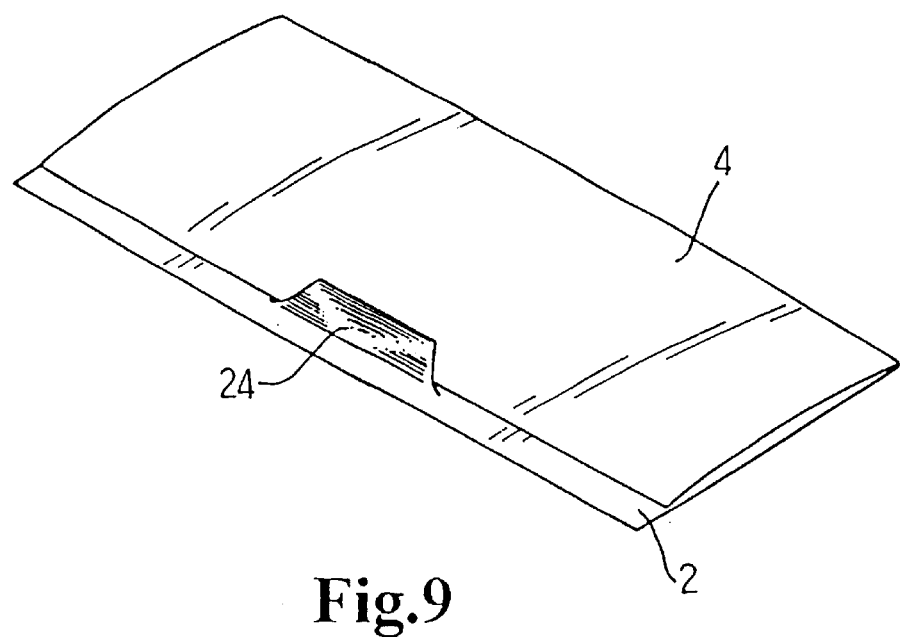
FIG. 9 is a perspective folded view of the third embodiment of the immunity testing device of the present invention, in which the covers are overlaying the base seat.
Figure 10:
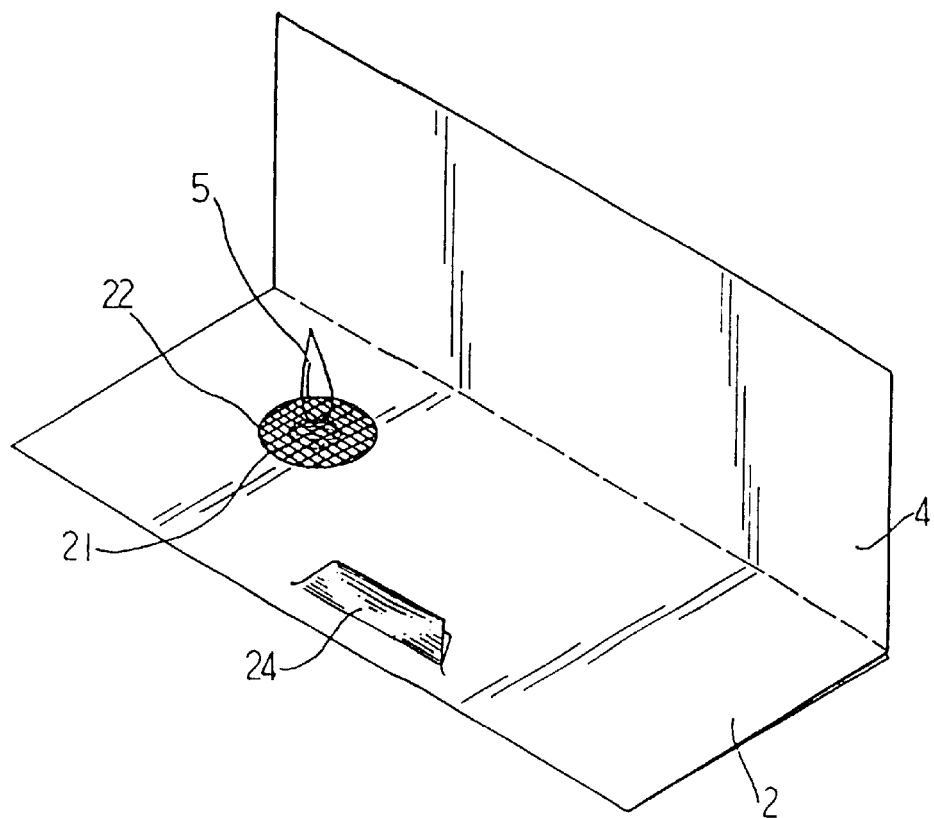
FIG. 10 is a perspective view of the third embodiment of the immunity testing device of the present invention, in which the back cover is unfolded from the base seat.
Figure 11:
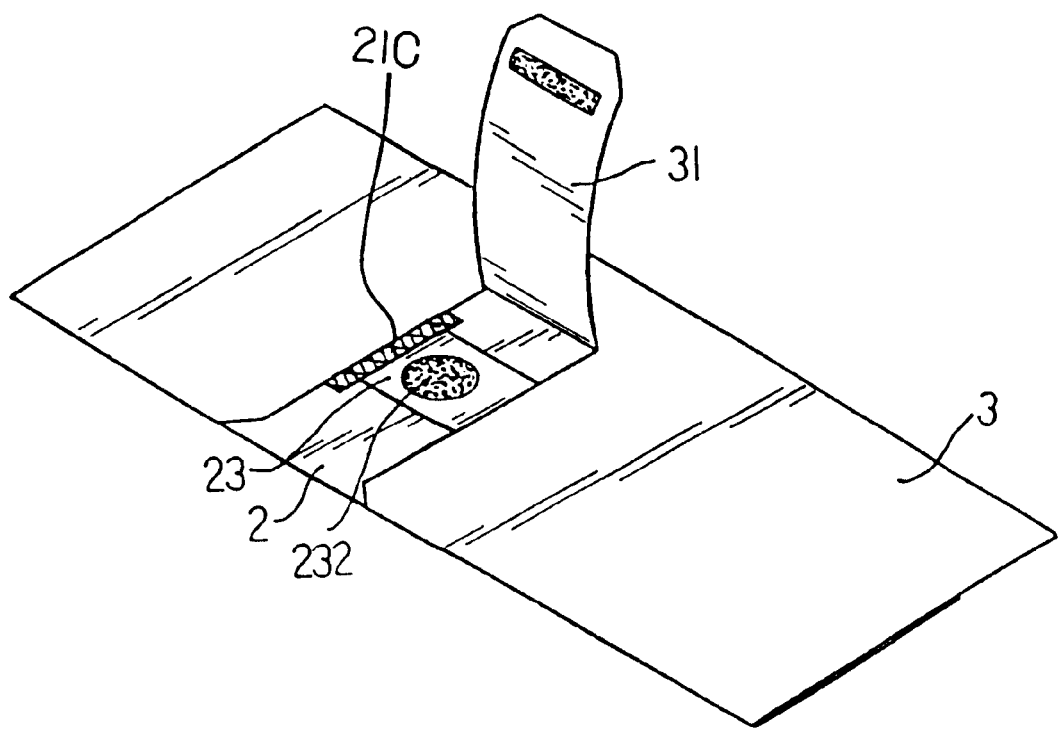
FIG. 11 is a perspective view of the third embodiment of the immunity testing device of the present invention, in which the observation cover plate in unfolded from the base seat.
Figure 12:
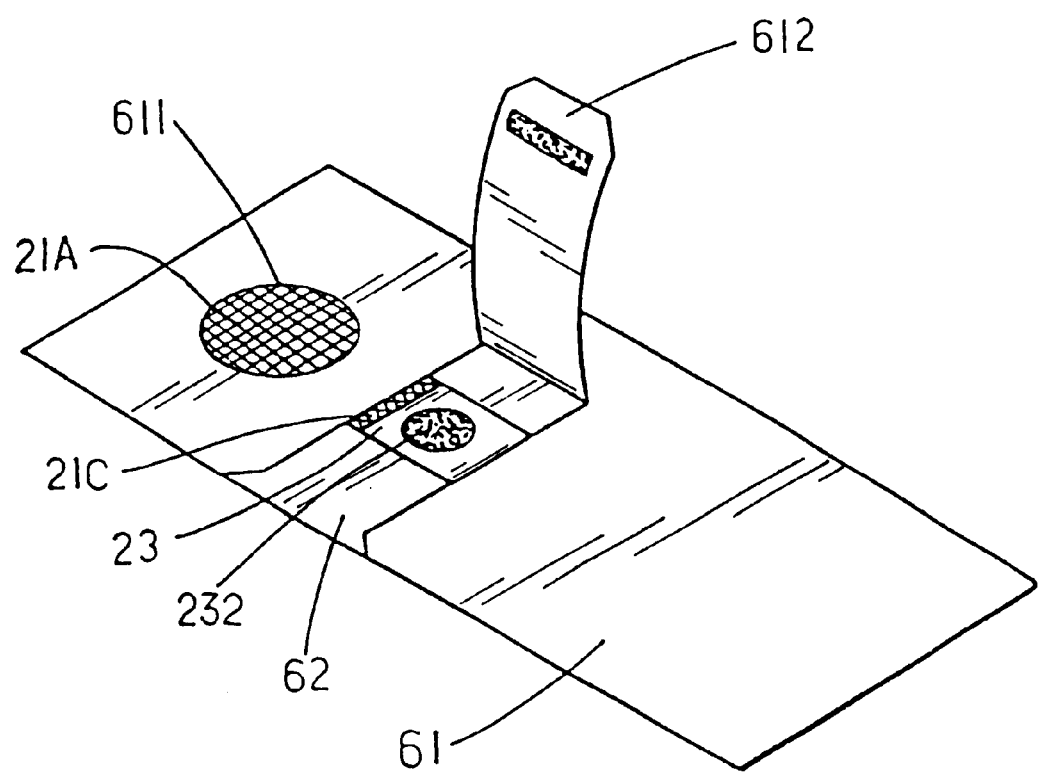
FIG. 12 is a perspective view of a fourth embodiment of the immunity testing device of the present invention, in which the observation cover plate is unfolded from the base seat.
Figure 13:
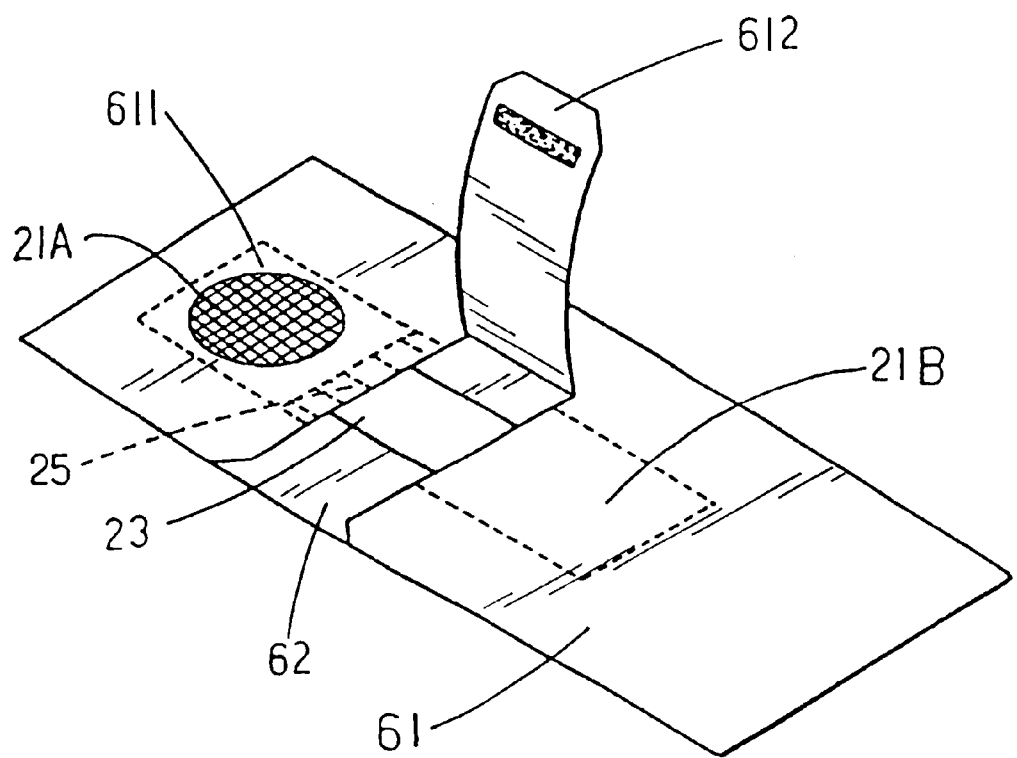
FIG. 13 is a perspective view of a fifth embodiment of the immunity testing device of the present invention, in which the observation cover plate is unfolded from the base seat.

As shown in FIGS. 6 and 7, alternatively, the present invention can be designed with a single folding pattern. That is, one single front cover 61 is overlaying the base seat 62. Two ends of the base seat 62 are respectively disposed with a first and a second water-absorbing sheets 21A, 21B interconnected by a test paper 23. The front cover 61 is formed with a dripping hole 611 at a position corresponding to the first water-absorbing sheet 21A and disposed with an observation cover plate 612 at a position corresponding to the test paper 23. Antibodies or antigens are embedded on the test paper 23 (The coating area can be in any desired readable shape.) When the test sample is applied through the dripping hole 611, the test sample is absorbed by the first water-absorbing sheet 21A and diffuses through the test paper 23 to the second water-absorbing sheet at the other end. During this period, in the case that the test sample contains an target element (such as human Hb), it will be bound on the antibody or antigen embedded on the test paper 23. Then the test agent is dripped on the test paper 23. After a specific reaction time, a user can observe whether the test paper 23 has a development of change which is an index of test result. This is the single monoclonal immunity test method. Simultaneously, when dripping the test agent, the user can also drip a chemical test agent through the dripping hole 611 to directly observe whether there is a development of change for chemical method test. Accordingly, the present invention is able to achieve dual reaction results of both immunological assay and chemical test As shown in FIG. 12, in the single folding pattern of the present invention, the first water-absorbing sheet 21A can also be extended towards the test paper 23 as part 21C to show under the area of the observation cover plate 612. A test agent is directly dripped onto the test paper 23 to diffuse into 21C for reaction with the test sample directly, this achieves the chemical test result. Furthermore, as shown in FIG. 13, labeled antigens or antibodies 25 (the label can be enzyme colored particle or fluorescent material) can be previously located into the first water-absorbing sheet 21A. After the test sample is dripped, the labeled antigens or antibodies 25 will combine with the target element in sample, this labeled compound will further diffuse into area 23, and bind with the pre-embedded antigen/antibody for "sandwich compounds" formation or undergo "competitive immunological binding". The sandwich and competitive compound will show visible changes on test paper 23 without further test step, which is called the "Direct Immunity Assay"; or an index reagent can be added to area 23 to develop visible changes for test result, and it is called the "Indirect Immunity Assay".

The chemical assay can be achieved by adding reagent directly on area 611. Again, it accomplishes the "dual method" task for the test in one test kit with simple performance.

Alternatively, as shown in FIG. 12, the first water-absorbing sheet 21A can be also elongated to extend toward the test paper 23 by a certain length 21C. A test agent is directly dripped onto the test paper 23 to diffuse and react on the extending portion 21C for the observation of chemical method.

The entire body of the present invention is made of flexible thin sheet material, which can be easily carried, used and stored without trouble.

Moreover, to simplify the manufacturing procedure, a length of the reaction strip, namely absorbent 21A & 21B bridged with test paper 23, can be first mounted on a thin layer of substrate (not illustrated) for the convenience of small partition. The desired size of reaction strip then can be adhered onto the base seat 2.

The antibodies or antigens previously located in the first water-absorbing shoot 21A can be modified in terms of its nature, quality and position as desired. Also, different antibodies or antigens can be simultaneously embedded on different positions of the test paper 23 for performing different nature of tests at the same time. Alternatively, the pattern and quantity of the embedded antibody or antigen can be adjusted in cooperation with the arrangement of quality control/comparison reaction test stripe.

It should be noted that the above description and accompanying drawings are only used to illustrate some embodiments of the present invention, not intended to limit the scope thereof. Any modification of the embodiments should fall within the scope of this present invention.

What is claimed is:

1. An immunity testing device comprising:
    a) a base having a base seat located between and integral with a front cover and a back cover, the base seat having first and second opposite facing surfaces;
    b) first and second absorbent sheets located on the first surface of the base seat, the first and second absorbent sheets being spaced apart from each other;
    c) a test paper located on the first surface of the base seat and in contact with the first and second absorbent sheets such that a liquid test sample applied to the first absorbent sheet will diffuse through the test paper to the second absorbing sheet;
    d) a hole in the base seat covered by the first absorbent sheet such that the first absorbent sheet is accessible through the hole from the second surface of the base seat;
    e) the front cover folded over and fixed to the first surface of the base seat so as to extend over the first and second absorbent sheets, the front cover having an observation area through which the test paper is exposed, the observation area being displaced from the hole;
    f) an observation cover plate formed in the front cover so as to be movable between an open position, in which the test paper is exposed through the observation area, and a closed position in which the observation cover plate covers the test paper;
    g) the back cover folded over onto the second surface of the base seat, so as to cover the hole; and,
    h) a releasable fastening device engaged by the back cover to releasably retain the back cover on the second surface of the base seat, the releasable fastening device enabling the back cover to be released and moved away from the second surface of the base seat to provide access to the hole whereby a liquid test sample may be applied to the first absorbent sheet.

2. The immunity testing device of claim 1 wherein the releasable fastening device comprises a tab formed integrally with the base seat which is releasably engagable by an edge of the back cover.

3. The immunity testing device of claim 1 wherein a portion of the first absorbent sheet is exposed through the observation area when the observation cover plate is in the open position.

4. The immunity testing device of claim 1 wherein the front cover is folded over and fixed to the first surface of the base seat by an adhesive.

5. The immunity testing device of claim 1 further comprising antibodies or antigens located in the first absorbent sheet.

6. The immunity testing device of claim 5 wherein the antibodies, or antigens located in the first absorbent sheet are labeled.

7. The immunity testing device of claim 6 wherein the labels are enzymes.

8. The immunity testing device of claim 6 wherein the label is a fluorescent material.

9. The immunity testing device of claim 6 wherein the labels are colored microparticles.

* * * * *